United States Patent
Jacobi

(10) Patent No.: US 8,348,459 B2
(45) Date of Patent: Jan. 8, 2013

(54) SURGICAL LIGHT

(75) Inventor: Leif Jacobi, Tuttlingen (DE)

(73) Assignee: Berchtold Holding GmbH, Tuttlingen (DE)

( * ) Notice: Subject to any disclaimer, the term of this patent is extended or adjusted under 35 U.S.C. 154(b) by 180 days.

(21) Appl. No.: 12/878,869

(22) Filed: Sep. 9, 2010

(65) Prior Publication Data

US 2011/0069485 A1 Mar. 24, 2011

(30) Foreign Application Priority Data

Sep. 21, 2009 (DE) .......................... 10 2009 042 338

(51) Int. Cl.
*F21V 11/00* (2006.01)

(52) U.S. Cl. ........ 362/241; 362/240; 362/247; 362/297; 362/346

(58) Field of Classification Search ................. 362/804, 362/231, 240, 241, 247, 248, 297, 298, 301–305, 362/346

See application file for complete search history.

(56) References Cited

U.S. PATENT DOCUMENTS

| | | | |
|---|---|---|---|
| 4,196,460 A | | 4/1980 | Schreckendgust |
| 4,745,526 A | * | 5/1988 | Sestak .............................. 362/35 |
| 5,136,483 A | * | 8/1992 | Schoniger et al. ............ 362/545 |
| 6,332,701 B1 | * | 12/2001 | Yamada et al. ................ 362/517 |
| 6,830,364 B2 | * | 12/2004 | Ter-Oganesian .............. 362/518 |
| 7,506,985 B2 | * | 3/2009 | Radominski et al. ........... 353/94 |
| 7,530,712 B2 | * | 5/2009 | Lin et al. ........................ 362/247 |
| 7,559,664 B1 | * | 7/2009 | Walleman et al. ............... 362/84 |
| 2004/0145910 A1 | * | 7/2004 | Lisowski ....................... 362/519 |
| 2005/0281048 A1 | * | 12/2005 | Coushaine et al. ........... 362/555 |
| 2008/0144328 A1 | | 6/2008 | Yagi et al. |
| 2008/0225541 A1 | * | 9/2008 | Ishida et al. .................. 362/516 |
| 2008/0304281 A1 | | 12/2008 | Scholz |
| 2009/0122536 A1 | | 5/2009 | Scholz |

FOREIGN PATENT DOCUMENTS

| | | |
|---|---|---|
| DE | 29 27 812 A1 | 1/1980 |
| DE | 60107297 T2 | 1/2004 |
| DE | 10 2005 036 275 A1 | 2/2007 |
| DE | 10 2007 061 304 A1 | 6/2008 |
| EP | 1 152 187 B1 | 7/2001 |

OTHER PUBLICATIONS

Search Report dated Jun. 21, 2010 in corresponding German Patent Application No. DE 102009042338.9 entitled "Surgical Light", 4 pages.
English Translation of Search Report dated Jun. 21, 2010 in corresponding German Patent Application No. DE 102009042338.9 entitled "Surgical Light", 5 pages.

* cited by examiner

*Primary Examiner* — John A Ward
(74) *Attorney, Agent, or Firm* — Lewis and Roca LLP

(57) ABSTRACT

A surgical light has a plurality of LEDs and a main reflector which directs the light of the LEDs onto an operating field. The main reflector is made in areal form and is divided into a plurality of reflector zones.

13 Claims, 4 Drawing Sheets

SURGICAL LIGHT

CROSS-REFERENCE TO RELATED APPLICATIONS

This application claims priority to co-pending German Patent Application Serial Number 10 2009 042 338.9, filed Sep. 21, 2009, the entirety of which is incorporated by reference herein.

BACKGROUND OF THE INVENTION

1. Field of the Invention

The present invention relates to a surgical light with a reflector and a light source having a plurality of LEDs.

2. The Prior Art

Surgical lights which generate the light to be directed to the operating field with the help of LEDs are known in practice. What is problematic with known surgical lights of this type is, on the one hand, the heat development of the LEDs and, on the other hand, the uniform illumination of the operating field without colored shadow and without cast shadow formation.

BRIEF DESCRIPTION OF THE INVENTION

It is the object of the present invention to further develop a surgical light with LEDs such that, with good thermal dissipation, a uniformly lit illuminated field can be produced which has as good as no shadow formation when a portion of the light incident onto the operating field is shaded by the surgeon.

This object is satisfied by the features of claim 1 and in particular by a surgical light with a light source which has a plurality of LEDs and a main reflector which has an optical axis and an outer margin and which directs the light of the LEDs onto an operating field. In accordance with the invention, the main reflector is made in areal fashion, with the LEDs being arranged and oriented such that their light is coupled into the main reflector from the outer margin thereof. In other words, no LEDs are arranged between the main reflector and the operating field so that the total surface of the main reflector can be used to illuminate the operating field. An areal design is understood in this context such that the reflector is not composed of individual reflectors. A stepped or facetted design is, however, e.g., considered as in accordance with the invention. The LEDs of the light source are furthermore spatially arranged at the outer margin of the reflector so that good thermal dissipation can be ensured. Since a plurality of LEDs can be coupled into the main reflector from the outer periphery of the main reflector, a high luminance can be achieved and the total main reflector can be uniformly illuminated with a plurality of light sources.

In accordance with the invention, the LEDs (light-emitting diodes) are arranged in ring shape and in particular in circular shape at the outer margin of the reflector. It is understood by this that the LEDs are peripherally arranged at the periphery of the surgical light or of the lamp body. In this respect, oval, elliptical or also quadrangular geometries can e.g. also be considered for the main reflector or for the arrangement of the LEDs. A particularly uniform illumination can, however, be achieved with a circular arrangement.

Advantageous embodiments of the invention are described in the description, in the drawings and in the dependent claims.

In accordance with an advantageous embodiment, the LEDs can be arranged so that their light is coupled into the main reflector via at least one coupling reflector. In this embodiment, it is not necessary that the direction of radiation of the LEDs is directed radially or approximately radially to the optical axis of the main reflector. The light-emitting diodes can rather be arranged such that their radiation axes extend parallel or approximately parallel to the optical axis of the main reflector, which can contribute to a compact design of the light fixture and, on the other hand, allows an improved thermal dissipation of the LEDs in the direction of the light fixture side disposed opposite the light exit area.

The coupling reflector can, in accordance with a further advantageous embodiment, be a ring reflector which is arranged in the region of the outer margin of the main reflector or which is formed in one piece with the main reflector. In the last-named embodiment, the main reflector can be provided with openings by which the light of the LEDs is radiated from the rear of the main reflector onto the coupling reflector and from there onto the main reflector.

In accordance with a further advantageous embodiment, the light of the LEDs can be coupled into the main reflector from its outer margin in the direction of the optical axis of the main reflector. It is alternatively possible also to radiate the light at an angle to the optical axis of the main reflector.

The main reflector can be divided into individual segments or zones or also facets, with the transition between adjacent segments being able to extend (in the mathematical sense) discontinuously or also continuously. In accordance with a further advantageous embodiment, in this respect individual zones (facets) of the main reflector can be divided into at least two groups, with each group of reflector zones imaging the incident light onto a different focusing plane. Different reflector zones are hereby created for different working distances and a much improved depth illumination is achieved with respect to conventional surgical lights.

To minimize the occurrence of colored shadows, LEDS with different color temperatures can be arranged alternately along the outer margin of the main reflector, with in particular a total of two different color temperatures being able to be provided, for example 10,000 K and 2,500 K. In this embodiment, in comparison with known surgical lights with LEDs, colored shadows are practically prevented since in this case different spectral portions are radiated into the illuminated field at approximately the same angle.

LEDs, i.e. light-emitting diodes, in the sense of the present invention are understood as any desired light-emitting diodes with different colored light and white light portions and with or without a suitable optical attachment. They are also understood as multichip LEDs with different colored light and white light portions.

A particularly good reduction in colored shadows can be achieved in that the LEDs are arranged at the outer margin of the main reflector such that two respective LEDs with different color temperatures are in each case disposed diametrically opposite one another.

In accordance with a further advantageous embodiment of the invention, at least two groups of LEDs can be provided at the outer margin of the main reflector, with the angle of incidence of the LEDs of the first group and the angle of incidence of the LEDs of the second group toward the optical axis of the main reflector being of different magnitude. This can be realized, for example, by a radial spacing of the LEDs toward the optical axis of the main reflector of different sizes or by a different angular position of the LED light sources toward the axis of the main reflector. In both cases, the advantage results that two illuminated fields of different size are produced by the two groups and lie concentrically to one another. An adaptation of the size of the illuminated field by proportional crossfading of the two illuminated fields is hereby possible by dimming the two LED groups.

In accordance with a further advantageous embodiment, the main reflector can have a section between two reflector zones or also facets which is orientated so that no light of the LEDs is reflected. This section thus does not contribute to the lighting of the operating field, but can be used to reduce the height of the main reflector in that the lower margin of a facet subsequent at distal to a facet is offset in the direction of the operating field.

A preferred good illumination of the operating field can be achieved in that a free-formed reflector is used as a main reflector of which in particular a plurality of reflector zones illuminate one and the same illuminated field. In other words, a plurality of facets, which are each illuminated by different LEDs, can be directed onto one and the same illuminated field so that several hundred facets can be used to achieve a shadowless illumination of the operating field.

Finally, it can be advantageous to couple the light of the LEDs in strip shape into the main reflector from the outer margin thereof, for example with the help of a bitoric lens or of a combination of a reflector and a two-stage optical system.

The present invention will be described in the following purely by way of example with reference to advantageous embodiments and to the enclosed drawings. There are shown:

DETAILED DESCRIPTION

Figure 1:
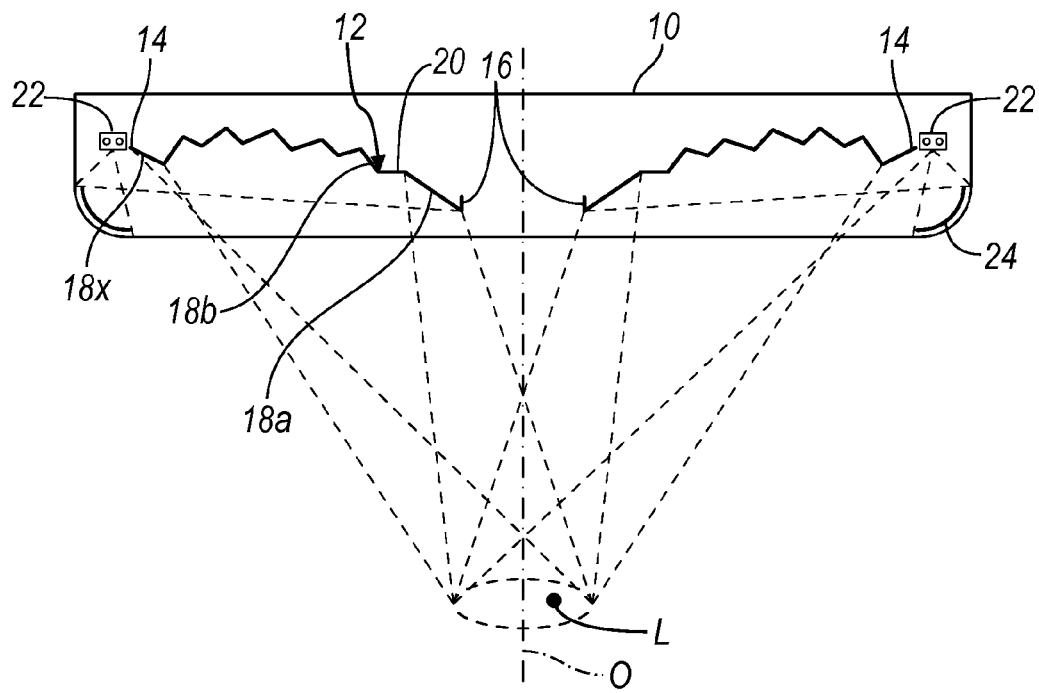
FIG. 1 a schematic cross-sectional view of a first embodiment of a surgical light.
Figure 7:
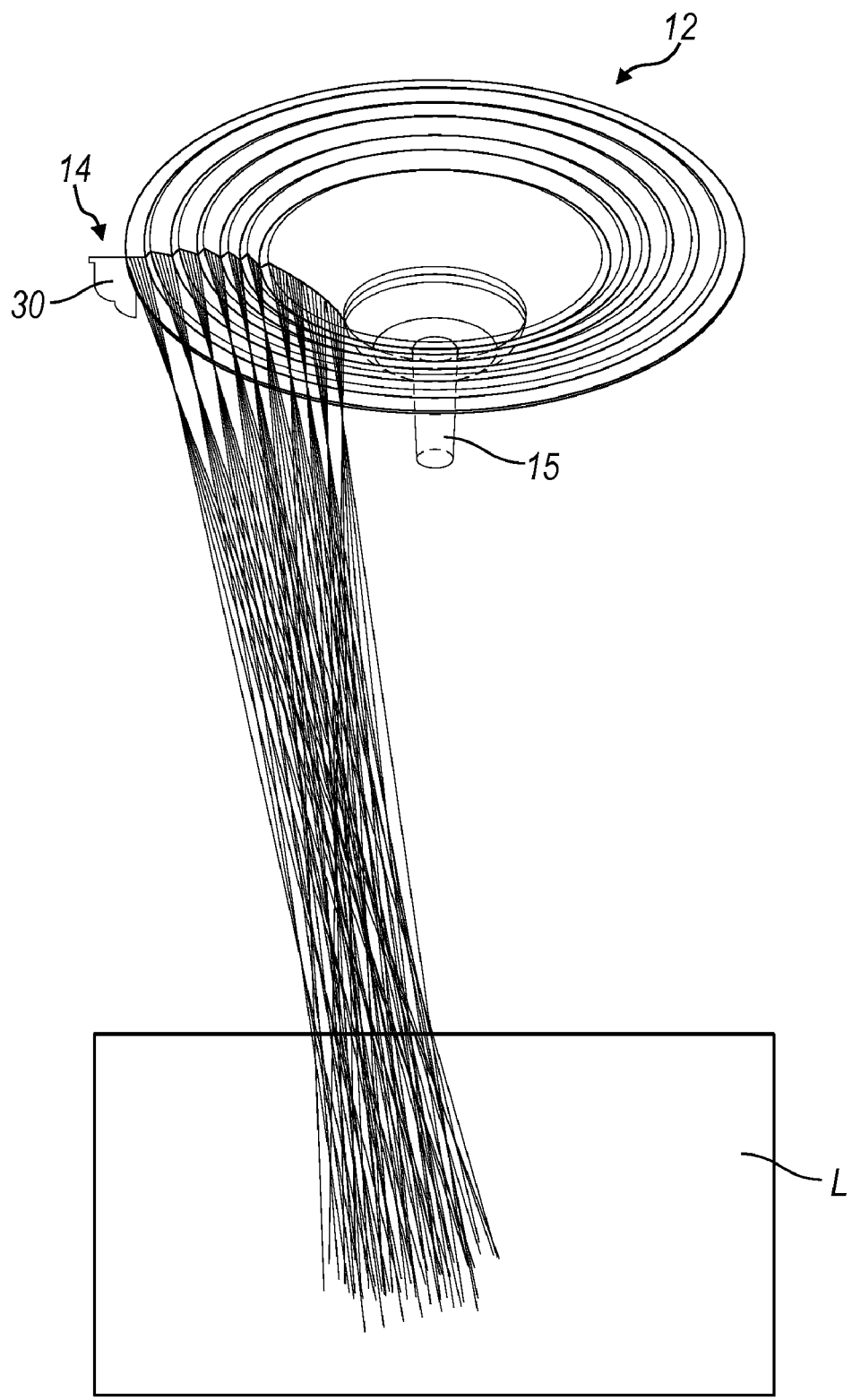
FIG. 7 a strip-shaped coupling of the LED radiation with overlapping of individual zone portions.

FIG. 1 shows a highly schematic cross-sectional view of a surgical light with a disk-like housing 10 in which a central main reflector 12 is arranged which has an optical axis O and an outer margin 14. In the embodiment shown, the main reflector 12 is made open in its central inner region so that this main reflector 12 also has an inner margin 16 which can be flowed through provided that corresponding throughflow openings are provided in the region of the housing 10. Alternatively, however, the main reflector 12 can also, as shown in FIG. 7, be made closed and have a central handle 15.

Figure 2:
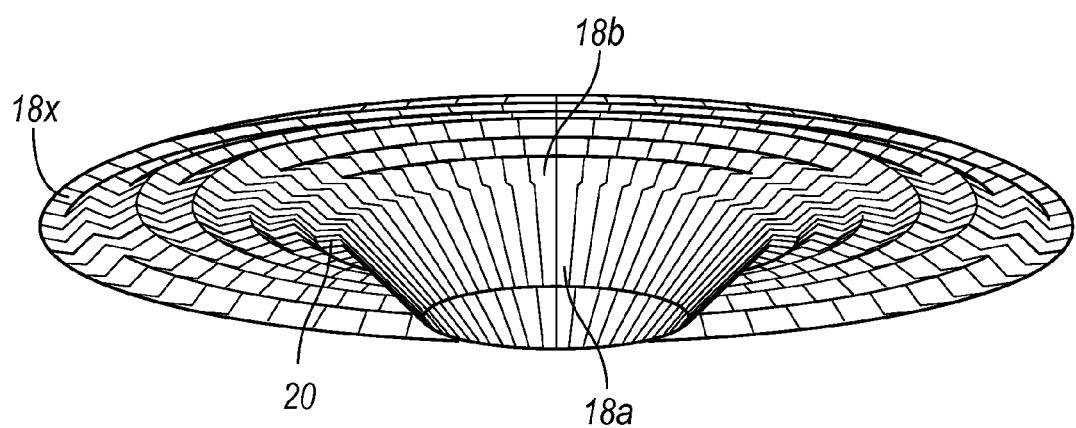
FIG. 2 a perspective view from below of the main reflector of the embodiment of FIG. 1.

The main reflector 12 shown in FIG. 1 and also in the other Figures is—in contrast to a ring reflector or individual reflectors—made in areal form (cf. FIG. 2) and it can—as in the embodiment shown) be divided into a plurality of reflector zones or facets 18a, 18b, . . . , 18x, with the main reflector being made as a free-formed reflector and the individual facets being able to merge continuously or discontinuously into one another. The main reflector can, for example, be a coated, injection molded part or as a stamped and/or drawn aluminum component.

To achieve the extremely flat construction of the main reflector 12 shown in the Figures, a section 20 is provided between two facets 18a and 18b adjacent along the optical axis which is orientated such that no incident light is reflected. The section 20 thus does not contribute to the illumination of the illuminated field, but allows a flat construction of the main reflector 12 since the lower margin, i.e. the margin of the facet 18b facing in the direction of the operating field is offset in the direction of the operating field along the optical axis O.

The surgical light shown has a light source in the form of a plurality of LEDs 22 which are arranged in ring shape in the region of the outer margin 14 of the main reflector 12, i.e. which are arranged peripherally at the periphery of the reflector and which couple their light into the main reflector from the outer margin 14 thereof. In the embodiment shown, however, the coupling of the light of the LEDs 22 does not take place directly, but rather indirectly via at least one coupling reflector. In the embodiment shown, a ring-shaped coupling reflector 24 is used which reflects the light radiated by the LEDs 22 arranged in ring shape approximately parallel to the optical axis O and couples it substantially transversely to the optical axis O laterally into the main reflector 12. In this respect, the geometry of the main reflector 12 is configured such that a plurality of facets 18a, 18b, . . . , 18x light one and the same illuminated field L. Since a plurality of facets are thus lit by a plurality of LEDs, the illuminated field L is also not in shadow when a portion of the light radiated by the main reflector 12 is shaded by the surgeon. Alternatively, however, the coupling into the main reflector can also take place via individual coupling reflectors. Such an embodiment is described in more detail below in connection with FIG. 6.

To reduce colored shadows, LEDs with different color temperatures, for example 10,000 K and 2,500 K, can be arranged alternately along the outer margin 14 of the main reflector 12, with preferably a total of only two different color temperatures being alternately provided. A considerable reduction in colored shadows is hereby achieved, with this being able to be further improved in that two diametrically opposed LEDS 22 at the outer margin 14 of the main reflector 12 each have different color temperatures. Alternatively or additionally, it is possible to use multichip LEDs with different colored light and white light portions, including a suitable optical attachment, as the LEDs 22.

Figure 3:
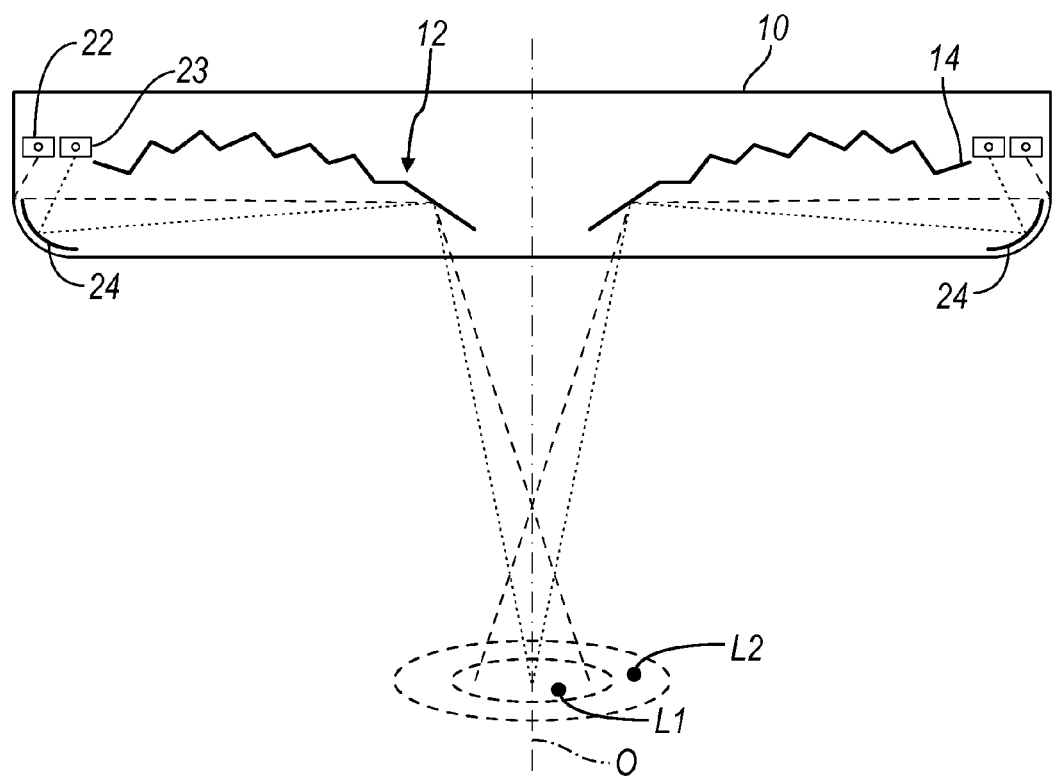
FIG. 3 a schematic cross-sectional view of a further embodiment of a surgical light.
Figure 5:
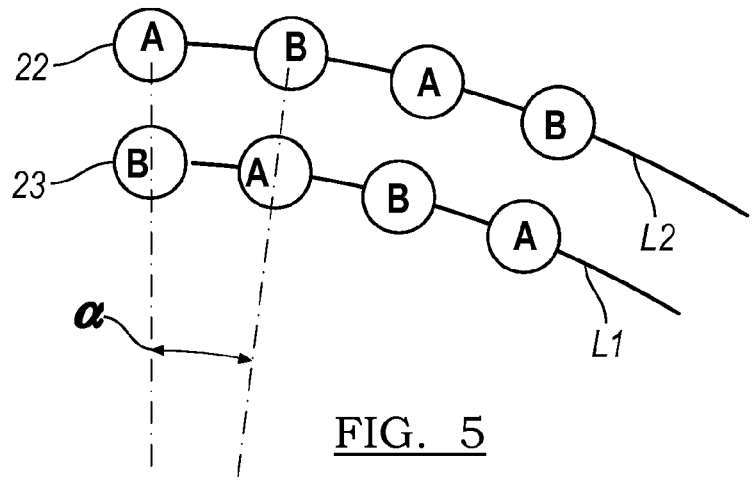
FIG. 5 a distribution of LEDs with different color temperatures along the periphery of the surgical light.

FIG. 5 shows such an alternating arrangement of LEDs with different color temperatures. In the embodiment shown, a total of only two different color temperatures A and B, for example cool white and warm white, with the two color temperatures alternating considered along the periphery. Viewed in the radial direction, two respective different color temperatures are likewise arranged behind one another. The angular spacing a between two adjacent LEDs can amount to approximately 6°. The illuminated field L1 is formed by the inner ring of LEDs arranged next to one another and shown in FIG. 5 and the illuminated field L2 is formed by the outer ring of LEDs. A surgical light having such an arrangement of LEDs is described in more detail in the following in connection with FIG. 3. FIG. 3 shows an embodiment of a surgical light which essentially corresponds to that of FIG. 1, with a variation in the size of the illuminated field L being able to be carried out, however, in the embodiment shown in FIG. 3. In the embodiment of FIG. 3, the same components are labeled with the same reference numerals and the corresponding components are not separately described again.

In the embodiment shown in FIG. 3, in addition to the ring of LEDs 22, a further concentric ring of LEDs 23 is arranged, with the LEDs 22 being arranged at a spacing from the optical axis O which is larger than the spacing of the LEDs 23 from the optical axis O. The light of the LEDs 22 and 23 is, however, directed to one and the same facets, with the angle of incidence of the light, however, being different both into the coupling reflector 24 and from the coupling reflector 24 into the main reflector 12 for the two groups of LEDs 22 and 23. An illuminated fields L1 or L2 of different sizes can thus be produced by a dimming of either the first group of LEDs 22 and/or of the second group of LEDs 23 so that an adaptation of the size of the illuminated field can take place without any mechanical movement.

The housing 10 of the surgical lights described above can be made either flat and in disk shape as shown. However, it can also be able to be flowed through at its center. The main reflector can either have the shape shown or can have the shape of a Frisbee or of a hub cap. Angular shapes or oval geometries are also possible.

Since the facets of the main reflector 12 are divided into a plurality of groups, with each group imaging the incident light onto a different focusing plane, approximately the same light conditions also result in each case at different working distances from the surgical light. The distance of the surgical light from the operating field can hereby also be varied, without the light conditions substantially changing.

Figure 4:
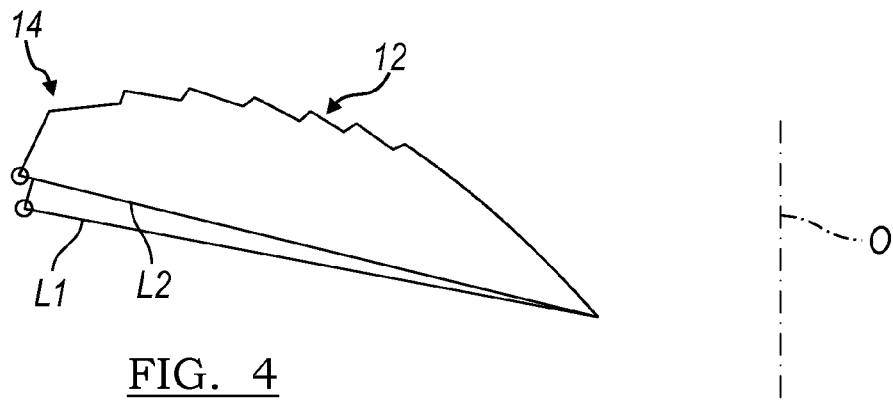
FIG. 4 a coupling at different angles to generate two illuminated fields.

FIG. 4 purely schematically illustrates how two overlapping illuminated fields can be created by coupling light into the main reflector 12 at different angles. In the embodiment shown, light is coupled into the main reflector 12 at respective different angles in the region of the outer margin 14 of the main reflector, whereby the created illuminated fields L1 and L2 overlap.

Figure 6:
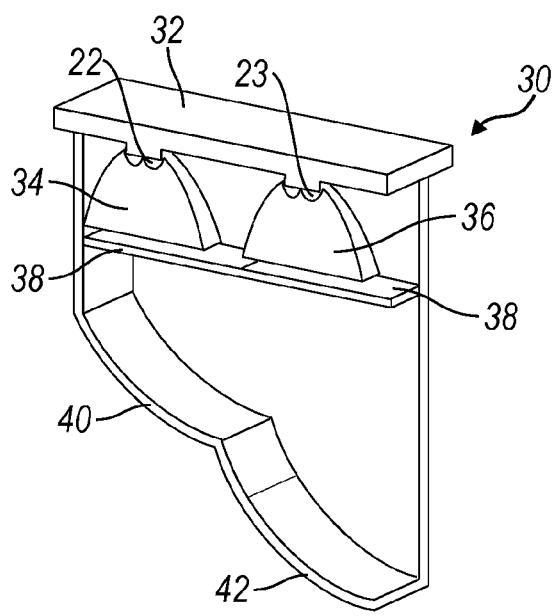
FIG. 6 a partly cut-away perspective view of an optical module.

FIG. 6 shows, as an alternative construction to the arrangement shown in FIG. 3, an optic module 30 which has an LED board 32 on which two light-emitting diodes 22 and 23 are arranged next to one another and directing the radiation vertically downwardly. The radiation of the light-emitting diodes is then directed via a primary optical system 34 36, for example via a plastic lens, via a respective filter 38 vertically downwardly onto a respective associated coupling reflector 40, 42, with each coupling reflector 40, 42 coupling the light of the associated LED 22 and 23 into the main reflector 12 from the outer periphery thereof.

The optic module shown in FIG. 6 can, for example in the embodiment of FIG. 3, be arranged at the outer margin 14 of the main reflector 12 and can there replace the LEDs 22, 23 as well as the ring reflector 24. Sixty optic modules can then, for example, be arranged along the periphery of the main reflector 12.

The coupling of an individual optic module, as is shown in FIG. 6, is shown schematically in FIG. 7. It can be recognized that a coupling of the radiation from the outer periphery of the main reflector 12 along a radial strip takes place by a single optic module 30, with the individual reflector zones or facets of the main reflector 12 reflecting the incident radiation downwardly onto the illuminated field L which overlaps in so doing.

I claim:

1. A surgical light, comprising
a light source which has a plurality of LEDs (22, 23); and
a main reflector (12) which has an optical axis (O) and an outer margin (14) and which directs the light of the LEDs (22, 23) onto an operating field,
wherein
the main reflector (12) is made in areal form;
the light of the LEDs (22, 23) is coupled into the main reflector (12) from the outer margin (14) thereof; and
the LEDs (22, 23) are arranged in ring shape, in particular in circular shape, at the outer margin (14) of the main reflector (12);
the main reflector (12) is divided into a plurality of reflector zones (18a, 18b, ..., 18x) which in particular light one and the same illuminated field (L, L1, L2); and wherein the reflector zones (18a, 18b, ..., 18x) are divided into at least two groups, with each group imaging the incident light onto a different focusing plane.

2. A surgical light in accordance with claim 1, characterized in that the light of the LEDs (22, 23) is coupled into the main reflector (12) via at least one coupling reflector (24, 40, 42).

3. A surgical light in accordance with claim 2, characterized in that the coupling reflector is a ring reflector (24) which is in particular made in one piece with the main reflector (12).

4. A surgical light in accordance with claim 2, characterized in that a plurality of discrete coupling reflectors (40, 42) are provided.

5. A surgical light in accordance with claim 2, characterized in that the main reflector (12) is provided with openings through which the light of the LEDs (22, 23) is radiated onto the at least one coupling reflector.

6. A surgical light in accordance claim 1, characterized in that the light of the LEDs (22, 23) is coupled into the main reflector (12) from its outer margin (14) in the direction of the optical axis (O).

7. A surgical light in accordance with claim 1, characterized in that LEDs (22, 23) with different color temperatures (A, B) are arranged alternately along the outer margin (14) of the main reflector (12), with in particular a total of two different color temperatures being provided.

8. A surgical light in accordance with claim 1, characterized in that at least two LEDs (22, 23) are provided at the outer margin (14) of the main reflector (12) whose light is coupled into the main reflector at different angles.

9. A surgical light in accordance with claim 1, characterized in that the main reflector (12) has a section (20) between two reflector zones (18a, 18b) which is orientated such that no light of the LEDs is reflected.

10. A surgical light in accordance with claim 1, characterized in that no LEDs (22) are arranged between the main reflector (12) and the operating field.

11. A surgical light in accordance with claim 1, characterized in that the main reflector (12) is a free-formed reflector.

12. A surgical light, comprising:
a light source which has a plurality of LEDs (22, 2); and
a main reflector (12) which has an optical axis (O) and an outer margin (14) and which directs the light of the LEDs (22, 23) onto an operating field,
wherein
the main reflector (12) is made in areal form;
the light of the LEDs (22, 23) is coupled into the main reflector (12) from the outer margin (14) thereof;
the LEDs (22, 23) are arranged in ring shape, in particular in circular shape, at the outer margin (14) of the main reflector (12);
a first ring of LEDs (22, 23) is provided, said LEDs having different color temperatures (A, B) arranged alternately along the outer margin (14) of the main reflector (12), with in particular a total of two different color temperatures being provided; and wherein
a second concentric ring of LEDs (22, 23) is provided, said LEDs having different color temperatures (A, B) arranged alternately along the outer margin (14) of the main reflector (12), with in particular a total of two different color temperatures being provided,
two LEDs with different color temperatures (A, B) being arranged diametrically opposite one another at the outer margin (14) of the main reflector (12).

13. A surgical light, comprising:

a light source which has a plurality of LEDs (22, 2); and a main reflector (12) which has an optical axis (O) and an outer margin (14) and which directs the light of the LEDs (22, 23) onto an operating field, the main reflector being divided into individual facets, wherein the main reflector (12) is made in areal form;

the light of the LEDs (22, 23) is coupled into the main reflector (12) from the outer margin (14) thereof;

the LEDs (22, 23) are arranged in ring shape, in particular in circular shape, at the outer margin (14) of the main reflector (12); and wherein at least two LEDs (22, 23) are provided at the outer margin (14) of the main reflector (12) whose light is coupled into the main reflector at different angles;

at least two groups of LEDs being provided at the outer margin of the main reflector, an LED of the first group and an LED of the second group being located adjacent to one another as seen in a plane through the optical axis, light from the LED of the first group and the LED of the second group being coupled in a strip shape to a same one of the facets of the main reflector, with the angle of incidence of the LEDs of the first group and the angle of incidence of the LEDs of the second group toward the optical axis of the main reflector being of different magnitude.

* * * * *